(12) United States Patent
Carlisle

(10) Patent No.: US 6,543,149 B1
(45) Date of Patent: Apr. 8, 2003

(54) COORDINATE MEASURING SYSTEM

(75) Inventor: Keith Carlisle, Discovery Bay, CA (US)

(73) Assignee: The Regents of the University of California, Oakland, CA (US)

(*) Notice: Subject to any disclaimer, the term of this patent is extended or adjusted under 35 U.S.C. 154(b) by 39 days.

(21) Appl. No.: 09/690,930

(22) Filed: Oct. 17, 2000

Related U.S. Application Data
(60) Provisional application No. 60/168,555, filed on Dec. 2, 1999.

(51) Int. Cl.[7] .................... G01B 5/004; G01B 21/22
(52) U.S. Cl. ............................ 33/503; 33/706
(58) Field of Search .................... 33/503, 645, 706, 33/707, 708

(56) References Cited

U.S. PATENT DOCUMENTS

| | | | | |
|---|---|---|---|---|
| 4,776,701 A | * | 10/1988 | Pettigrew .................... | 356/356 |
| 5,061,073 A | * | 10/1991 | Michel ........................ | 33/707 |
| 5,120,132 A | * | 6/1992 | Spies et al. ................. | 356/356 |
| 5,333,386 A | * | 8/1994 | Breyer et al. ................ | 33/503 |
| 5,333,390 A | * | 8/1994 | Petterson et al. ............ | 33/706 |
| 5,386,642 A | * | 2/1995 | Spies et al. ................. | 33/708 |
| 5,511,321 A | * | 4/1996 | Nelle .......................... | 33/704 |
| 5,651,187 A | * | 7/1997 | Affa ............................ | 33/706 |
| 5,711,084 A | * | 1/1998 | Spanner ....................... | 33/706 |
| 5,793,201 A | * | 8/1998 | Nelle et al. .................. | 33/706 |
| 6,002,250 A | * | 12/1999 | Masreliez et al. ..... | 324/207.16 |
| 6,018,881 A | * | 2/2000 | Spies .......................... | 33/706 |
| 6,351,313 B1 | * | 2/2002 | Braasch et al. ............. | 33/707 |

OTHER PUBLICATIONS

"Exposed Incremental Two–Coordinate Measuring System PP201R," Heidenhain Corporation, Jul. 1996 ( 3 pages).*

* cited by examiner

*Primary Examiner*—G. Bradley Bennett
(74) *Attorney, Agent, or Firm*—James S. Tak; Alan H. Thompson

(57) ABSTRACT

An apparatus and method is utilized to measure relative rigid body motion between two bodies by measuring linear motion in the principal axis and linear motion in an orthogonal axis. From such measurements it is possible to obtain displacement, departure from straightness, and angular displacement from the principal axis of a rigid body.

48 Claims, 4 Drawing Sheets

COORDINATE MEASURING SYSTEM

This application claims the benefit of Provisional application Ser. No. 60/168,555, filed Dec. 2, 1999.

The United States Government has rights in this invention pursuant to Contract No. W-7405-ENG-48 between the United States Department of Energy and the University of California for the operation of Lawrence Livermore National Laboratory.

FIELD OF THE INVENTION

This application relates generally to measuring systems and more specifically relates to improving measurement capability by using a coordinate measuring system.

BACKGROUND OF THE INVENTION

Linear encoders are frequently used wherever high precision measurements are required. Linear encoders are often affixed to high precision, numerically controlled machine tools. A critical element of these machine tool designs are their measuring systems. The measuring system's resolution and accuracy must be adequate for the task and the positioning of the measuring system relative to the point of interest is important to avoid measurement errors. Lasers in a vacuum have been favored in the past because they represented the state-of-the-art in measurement capability. However, the cost of a laser system may be excessive.

SUMMARY OF THE INVENTION

Aspects of the present invention include a system comprising: a first periodic measurement scale assembly substantially aligned with a first axis; and a first plurality of sensors positioned substantially proximate to the first periodic measurement scale assembly, the first plurality of sensors including a pair of sensors spaced from each other along the first axis and configured to cooperatively measure at least one of departure from straightness of a first effective point from the first axis and angular displacement of the first effective point from the first axis.

Aspects of the present invention further include the first plurality of sensors having at least one sensor configured to measure linear displacement of a first effective point along the first axis.

Aspects of the present invention further include a second periodic measurement scale assembly substantially aligned with a second axis substantially orthogonal to the first axis; and a second plurality of sensors positioned in proximity to said second periodic measurement scale assembly, with the second plurality of sensors including at least one sensor configured to measure displacement of a second effective point along the second axis, and a pair of sensors spaced from each other along the second axis and configured to cooperatively measure at least one of departure from straightness of the second effective point from the second axis, and angular displacement of the second effective point from the second axis.

Aspects of the present invention further include measuring at least one of departure from straightness of a first effective point from a first axis and angular displacement of the first effective point from the first axis, by cooperatively utilizing a pair of sensors spaced from each other along the first axis and positioned substantially proximate a first scale assembly substantially aligned with the first axis.

Aspects of the present invention further include measuring linear displacement of the first effective point along the first axis by using at least one sensor positioned substantially proximate the first scale assembly.

Aspects of the present invention further include measuring displacement of a second effective point along a second axis using at least one sensor positioned substantially proximate a second scale assembly; measuring at least one of departure from straightness of the second effective point from the second axis and angular displacement of the second effective point from the second axis, by cooperatively using a pair of sensors spaced apart from each other long the second axis and positioned substantially proximate the second scale assembly.

Aspects of the present invention further include a first scale assembly having a plurality of first periodic measurement scales substantially aligned with a first axis; and a first plurality of pairs of sensors positioned in substantial proximity to said first scale assembly, said first plurality of pairs of sensors including a first pair of sensors spaced from each other along the first axis and configured to cooperatively measure departure from straightness of a first effective point from the first axis.

Aspects of the present invention further include a position measuring device comprising: a plurality of first periodic measurement scales substantially aligned with a first axis; and a first plurality of sensors positioned substantially proximate to said plurality of first periodic measurement scales, said first plurality of sensors including at least one sensor configured to measure linear displacement of a first effective point along the first axis, and a pair of sensors spaced from each other along the first axis and configured to cooperatively measure departure from straightness of the first effective point from the first axis, and angular displacement of the first effective point from the first axis.

Aspects of the present invention further include a machine tool comprising: a first scale assembly having a first periodic measurement scale aligned with a first axis; and a firs plurality of sensors positioned in proximity to said first scale assembly, said first plurality of sensors including a pair of sensors spaced from each other along the first axis and configured to cooperatively measure at least one of departure from straightness of a first effective point from the first axis and angular displacement of the first effective point from the first axis.

Aspects of the present invention further include a method of determining the position of a rigid body comprising: measuring linear displacement of a first effective point along a plurality of measurement scales substantially aligned along a first axis by cooperatively using a first pair of sensors positioned substantially proximate said plurality of measurement scales; and measuring at least one of departure from straightness of the first effective point from the first axis and angular displacement of the first effective point from the first axis, by cooperatively using a second pair of sensors spaced apart from each other along the first axis and positioned substantially proximate said plurality of measurement scales.

Aspects of the present invention further include an apparatus comprising: means for measuring at least one of departure from straightness and angular displacement of a first effective point from a first axis by cooperatively using a pair of sensors spaced from each other along said first axis and positioned substantially proximate a first scale assembly substantially aligned with said first axis.

Aspects of the present invention further include a measuring device comprising: means for measuring linear displacement of a first effective point along a plurality of measurement scales aligned along a first axis by using a first pair of sensors positioned substantially proximate said plurality of measurement scales; and means for measuring at least one of departure from straightness of the first effective point from the first axis and angular displacement of the first effective point from the first axis by cooperatively using a second pair of sensors positioned substantially proximate said plurality of measurement scales.

Aspects of the present invention further include a system comprising: first means for measuring a position of a rigid body relative to a reference body; and second means for measuring a position of an object relative to the reference body, with said object configured to act upon said rigid body wherein said second means is configured to compensate for errors in the position of the rigid body relative to the object.

Aspects of the present invention further include a system comprising: a first scale assembly substantially aligned with a first axis; a second scale assembly substantially aligned with a second axis; a first slide assembly having at least one sensor and designed to travel along and substantially proximate to said first scale assembly; a second slide assembly having at least one sensor and designed to travel along and substantially proximate to said second scale assembly, wherein one pair of the pair of scale assemblies and the pair of slide assemblies is fixed with respect to each other; and a control system configured to utilize data from said at least one sensor on said second slide assembly to compensate for errors in the positioning of a first effective point on the first slide assembly.

Aspects of the present invention further include a system comprising: a first scale assembly having a plurality of first periodic measurement scales substantially aligned with a first axis; a first plurality of pairs of sensors positioned substantially proximate to said first scale assembly said first plurality of pairs of sensors including at least one sensor configured to measure linear displacement of the first effective point along the first axis, and a pair of sensors spaced apart from each other and configured to cooperatively measure at least one of departure from straightness of a first effective point from the first axis and angular displacement of the first effective point from the first axis; a second scale assembly having a plurality of periodic measurement scales aligned with a second axis; a second plurality of pairs of sensors positioned substantially proximate to said second plurality of periodic measurement scales, said second plurality of pairs of sensors including at least one sensor configured to measure linear displacement of a second effective point along the second axis, and a pair of sensors spaced apart from each other and configured to cooperatively measure at least one of departure from straightness of the second effective point from the second axis, and angular displacement of the second effective point from the second axis; and wherein said second plurality of pairs of sensors are configured to compensate for errors in the positioning of a rigid body.

BRIEF DESCRIPTION OF THE DRAWINGS

The accompanying drawings, which are incorporated into and form a part of the disclosure.

DETAILED DESCRIPTION OF THE INVENTION

Disclosed herein is a system and method to measure relative rigid body motion by measuring linear motion in the principal axis and linear motion in the axes orthogonal to the principal axis. From these measurements it is possible to determine the relative position of a rigid body and a functional point on a rigid body. The functional point being the point of interest or, for example, the point where a tool would operate on the rigid body. The measuring system and method disclosed herein measures the displacement along a scale of an effective point which is offset from the functional point on the rigid body. The term offset is used in this disclosure to mean that the effective point and the functional point travel on different axes. The movement of the effective point corresponds to the displacement of the functional point and the term corresponds will mean for these purposes of this disclosure that the movement of the functional point will cause a substantially equivalent movement in the effective point.

In order to measure the position of a rigid body in relation to a slide assembly in a two coordinate plane, the following considerations are considered. First, in order to avoid errors in parallax, the path of the effective point of the measuring system should be placed collinear with the path of the functional point on the rigid body whose displacement is to be measured. Since this is not often possible, either the slide paths that transfer the displacement must be free of angular motion or angular motion data should be used to calculate the consequences of the offset. Second, the effective point of a straightness measuring system should lie along a line which is perpendicular to the direction of slide assembly way travel and passes through the functional point whose straightness is to be measured. If this is not possible, either the slide assembly paths that transfer the displacement must be free of angular motion or angular motion data must be used to calculate the consequences of the offset. Therefore, the embodiments of the measuring system disclosed herein calculate the angular motion data to compensate for or factor in the consequences of the offset of the functional point from the effective point in determining the position of the functional point and the rigid body.

Figure 1:
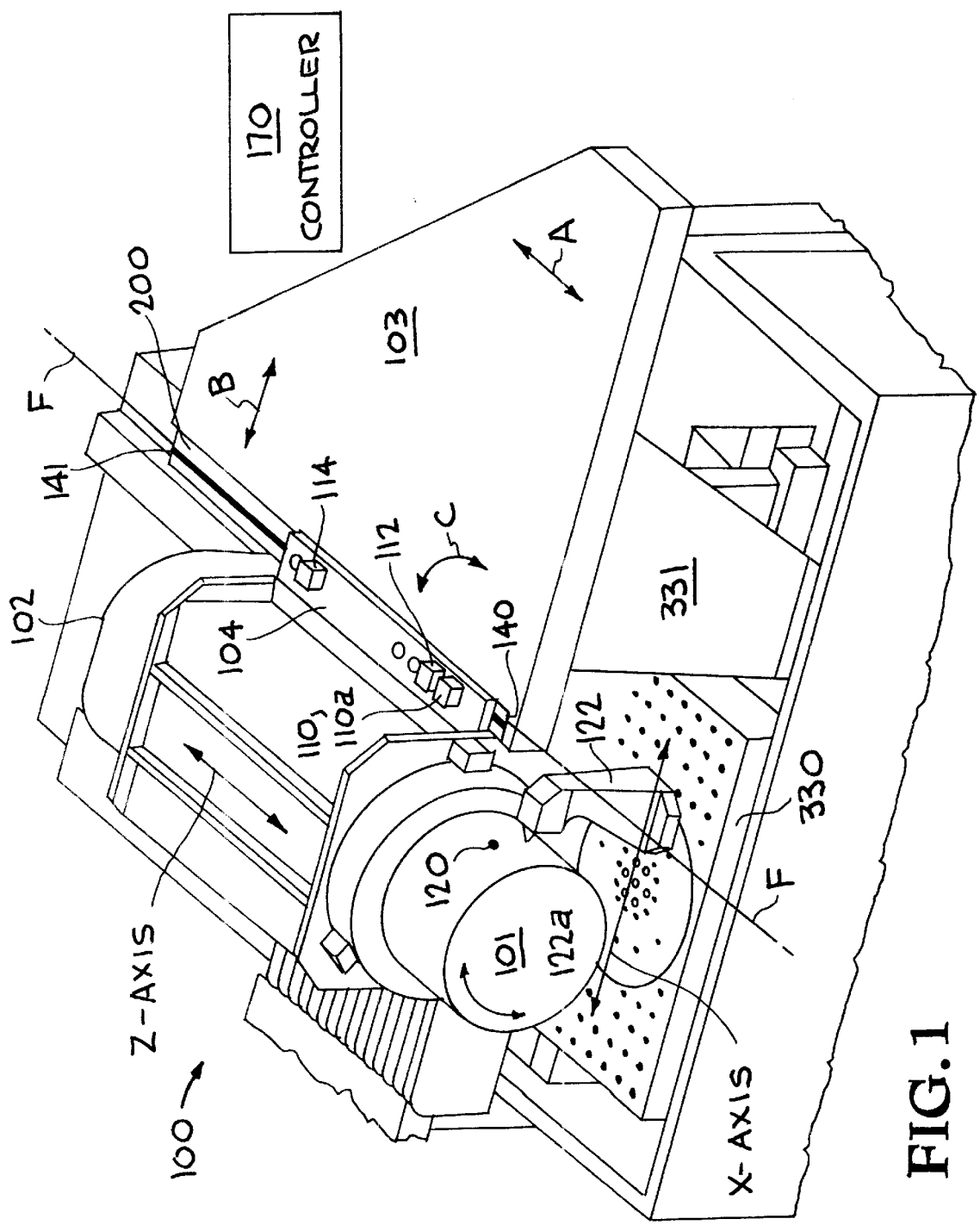
FIG. 1 illustrates a perspective view of a first embodiment of the present invention.

FIG. 1 illustrates a first embodiment of the present invention. FIG. 1 discloses a device 100 such as a machine tool. Reference numeral 170 indicates a controller which may be a system controller or a localized controller which contains software for performing calculations used in determining the position of a functional point and a rigid body (e.g., workpiece) 101. Also, coupled to the controller 170 are sensors 110, 112 and 114 (whose function is described below). Connections between the controller 170 and sensors 110, 112, and 114 are not shown. The rigid body 101 whose relative position is to be determined is placed substantially along a principal axis Z and substantially orthogonal to an axis X. The X and Z axes are orthogonal axes. Rigid body 101 is attached to a first mounting member 102. A first slide assembly 104 is mounted on the first mounting member 102 and first mounting member 102 translates (or correlates) the movements of the rigid body 101 to the first slide assembly 104. A functional point 120 is shown on the rigid body 101. As discussed above, functional point 120 is the point of interest that, for example, a tool post 122 and lathe tool 122a will operate upon and whose position the operator of the machine tool 100 is concerned. The tool post 122 is moveable to a predetermined position and rests on tool carriage assembly 330. In a first embodiment shown in FIG. 1, the tool carriage assembly 330 is fixedly connected to a reference base 103 by means of a connecting member 331.

An effective point 110a is located on the first slide assembly 104 at the position of sensor 110. The movement of the effective point (or measurement point) 110a along a unified, stationary first scale assembly 200 will correspond to the movement of the functional point 120 on the rigid body 101 and will allow the operator of the machine tool 100 to accurately monitor the position of the functional point 120. On top of the first slide assembly 104 are attached sensors 110, 112 and 114. In substantial proximity to the first slide assembly 104 is the first scale assembly 200 which is mounted on the reference base 103 of the device 100. First scale assembly 200 provides accuracy on a nanometric level in a relatively inexpensive manner. First scale assembly 200 lies along a first axis F which is substantially parallel to the principal axis Z. Using an offset methodology and monitoring the movements of the effective point 110a in relation to the first scale assembly 200 will allow the operator to determine the corresponding position of the functional point 120. (The offset calculations may use the Abbe offset in determining the relationship between the functional point and the effective point). The stationary first scale assembly 200 has a first end 140 and a second end 141.

During operation, first slide assembly 104 moves along axis F substantially parallel to principal axis Z along stationary scale assembly 200. First scale assembly 200 and first slide assembly 104 jointly measure the differential motion between the first scale assembly 200 and the first slide assembly 104 and determine the movement of the effective point 110a in relation to the first axis F. Relative movement is monitored by sensors 110, 112, and 114 mounted on the first slide assembly 104. Sensors 110, 112, and 114 measure data on the first scale assembly 200 such as gradations to determine displacement of the effective point 110a. Sensors 110, 112, and 114 may be any device that transmits a signal to a control instrument when then processes the data. Elements which meet this criteria include (but are not limited to) the following: transducers, read heads, photodetectors, or photosensors. Signal processing electronics and a system controller 170 (e.g., microprocessor, conventional circuitry, etc.) are connected to the sensors 110, 112, and 114 to determine the relative position of the slide assembly 104 on a nanometric level. Before operation, the location of the effective point 110a in relation to the sensors 110, 112, and 114 is entered into an offset algorithm in the controller 170. During operation, the controller 170 is configured to utilize the location data of the effective point 110a in conjunction with the dynamic data from the sensors 110, 112, and 114 to determine the corresponding position of the functional point 120 on rigid body 101.

The sensors 110, 112 and 114 cooperate to measure linear displacement of the functional point 120 along the principal axis Z by measuring linear displacement of the effective point 110a along the F axis, departure from straightness of the functional point 120 from the principal axis Z by measuring the departure from straightness of the effective point 110a from the F axis, and the angular displacement of the functional point 120 from the principal axis Z by measuring the angular displacement of the effective point 110a from the F axis. Linear displacement along the first axis F (shown by arrow A in FIG. 1) is the distance traveled by the effective point 110a on slide assembly 104 along the first axis F. Sensor 110 is configured to monitor this distance and send the data to controller 170. Departure from straightness measurement is the distance that the effective point 110a has moved orthogonally in relation to the first axis F (shown in FIG. 1 as arrow B). Angular displacement measurement is the angle that the effective point 110a on the slider assembly 104 has slanted off of the first axis F (shown by arrow C in FIG. 1). Sensors 112 and 114 monitor the orthogonal displacement on the first scale assembly 200 to determine the data required to calculate departure from straightness and angular displacement and report this data to controller 170 where the calculations take place.

As discussed above, with the measurement of linear displacement, departure from straightness and angular displacement of the effective point 110a, it is possible to determine the corresponding movements of the functional point 120 on the rigid body 101.

Figure 2:
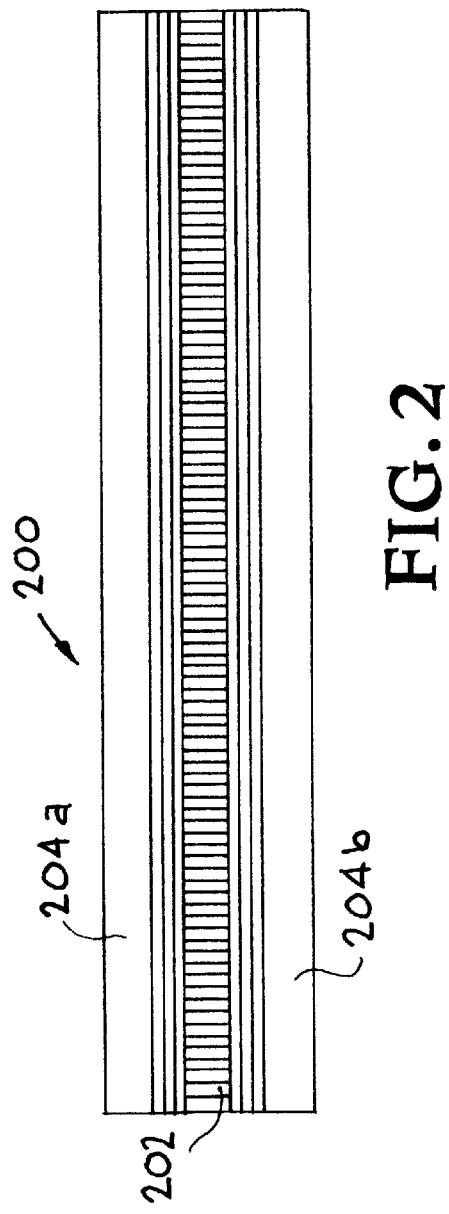
FIG. 2 illustrates a plan view of a unified scale assembly.

Unified first scale assembly 200 is shown in detail in FIG. 2.

Sensor 110 measures the displacement of the effective point 110a along the first axis F by monitoring the grades or gradations along section 202 of first scale assembly 200 as the first slide assembly 104 moves in axis F which is substantially parallel to the Z axis. The gradations 202 are substantially orthogonal to the first axis F and are used to measure displacement along the F axis. The data obtained by sensor 110 is sent to controller 170 which collects the data from sensors 110, 112 and 114. From this data, controller 170 determines the linear displacement of an effective point 110a along the F axis which represents the linear displacement of the functional point 120 along the Z axis. Gradations 204a and 204b of first scale assembly 200 are substantially parallel to the first axis F and are used to measure departure in an orthogonal direction from the first axis F by the effective point 110a. Sensors 112 and 114 monitor movement across gradations 204a and 204b on first scale assembly 200 to measure the departure from straightness and the angular displacement of the effective point 1110a. The photosensors 112 and 114 are spaced apart a distance D on the first slide assembly 104. By varying a placement distance D between the sensors 112 and 114, the sensitivity of angular measurement of the sensors 112 and 114 may be changed. The placement distance D between the two sensors 112 and 114 should be equal to, or greater than the separation of the functional point 120 from the effective point 110a. Placement distance D may, for example purposes, be approximately six inches. Sensor 112 monitors the gradations in sections 204a and 204b on both sides of first scale assembly 200 to obtain a first reading and photosensor 114 also monitors the gradations in sections 204a and 204b at a different point on first scale assembly 200 to obtain a second reading. To determine the departure from straightness from the first axis F, the first and second readings are sent to the controller 170 where the displacement from the first axis F, labeled B in FIG. 1, is determined. To determine the angular displacement from the first axis F, which is labeled C in FIG. 1, the first and second readings are sent to the controller 170 and the angular displacement is calculated by using the sensor separation distance D and the difference between the first and second readings. The controller 170 will use software containing standard algorithms to perform the calculations of the departure from straightness and the angular displacement from the first axis F.

As previously discussed, the calculations of the linear displacement, angular displacement and departure from straightness of the effective point 110a from the first axis F will determine the linear displacement, angular displacement and departure from straightness of the functional point 120 from the principal axis Z and allow precise determination of the position of the functional point 120 on the rigid body 101.

Figure 3:
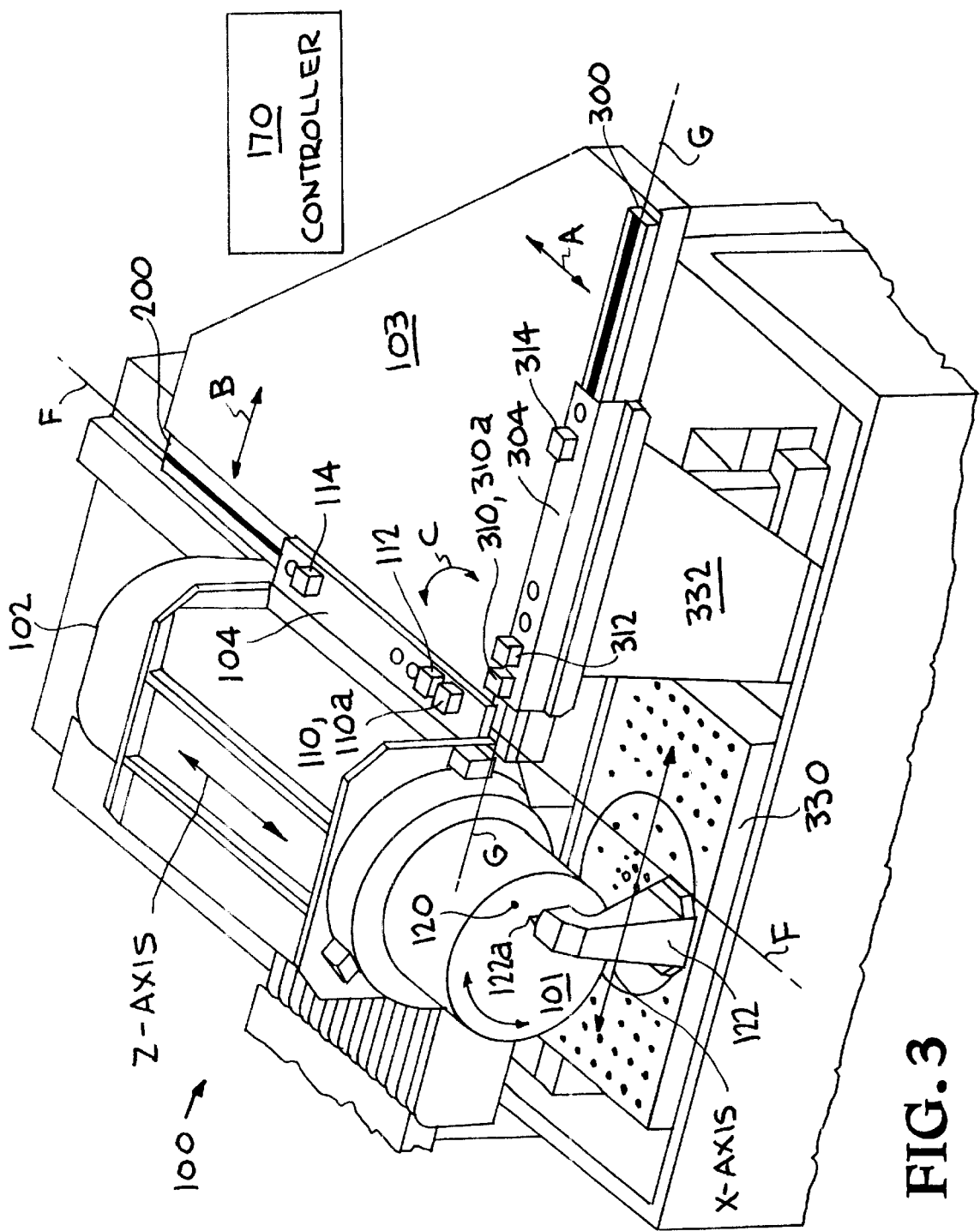
FIG. 3 illustrates a perspective view of a second embodiment of the present invention.

FIG. 3 illustrates a second embodiment of the present invention which further includes a second slide assembly 304 which travels along a second stationary scale assembly 300. Similar to the first scale assembly 200, the second stationary scale assembly 300 is also fixedly mounted on the reference base 103. Functional point 120 is shown in a different position on the rigid body 101 from that of FIG. 1. Second scale assembly 300 is substantially parallel to the X axis and lies along a second axis G. The use of the second slide assembly 304 and the second scale assembly 300 allows for compensation of errors in the position of the functional point 120 and rigid body 101 in relation to the tool detected by the first slide assembly 104 and first scale assembly 200. Controller 170 will alter the position of tool carriage assembly 330 and thus tool post 122 in response to data from the sensors on the first and second slide assemblies.

Second slide assembly 304 is similar in design to first slide assembly 104. However, instead of being attached to first mounting member 102, the second slide assembly 304 is attached to a second mounting member 332 (in FIGS. 3 and 4) which is connected to the tool carriage assembly 330 upon which rests tool post 122 and lathe tool 122a. Second mounting member 332 is not fixed with respect to the reference base 103, functioning instead to translate the movement of the tool post 122 and lathe tool 122a to the second slide assembly 304 for measurement against the reference base 103. Based on the measured position data of the functional point 120 on the rigid body 101 obtained from the first plurality of sensors 110, 112, and 114, the tool 122a may be positioned to compensate for the errors in positioning of the rigid body 101 in the orthogonal direction along the X axis. The tool 122a will compensate by moving to maintain a substantially constant distance from the functional point during operation. The second slide assembly 304 includes sensors 310, 312 and 314 which function in a manner similar to sensors 110, 112 and 114 to measure displacement, departure from straightness and angular displacement of a second effective point (or point of measurement) 310a from the second axis G. Second scale assembly 300 is similar in design to first scale assembly 200. Sensor 310 measures displacement along the G axis and spaced apart sensors 312 and 314, in combination, measure the departure from straightness from the G axis and angular displacement from the G axis.

The positioning of two scale assemblies 200 and 300, which are substantially orthogonal to each other, allows the true position of the functional point 120 on the moving rigid body 101 to be determined. Motion of the first slide assembly 104 is measured substantially in the F axis only (and correspondingly motion of the rigid body 101 is measured substantially in the Z axis only), all angle and straightness errors that lie in the orthogonal direction may only be measured and compensation must be made by the second slide assembly 304 substantially aligned with an axis orthogonal to the Z axis (and F axis). Therefore, the advantage of the use of two scale assemblies 200, 300 is that when applied to two orthogonal axes there is the ability to use the second slide assembly 304 in a synchronized manner to compensate for non-straightness of motion of the first slide assembly 104. This method may also be applied in reverse for compensation of errors in the second slide assembly 304 by the first slide assembly 104.

Figure 5:
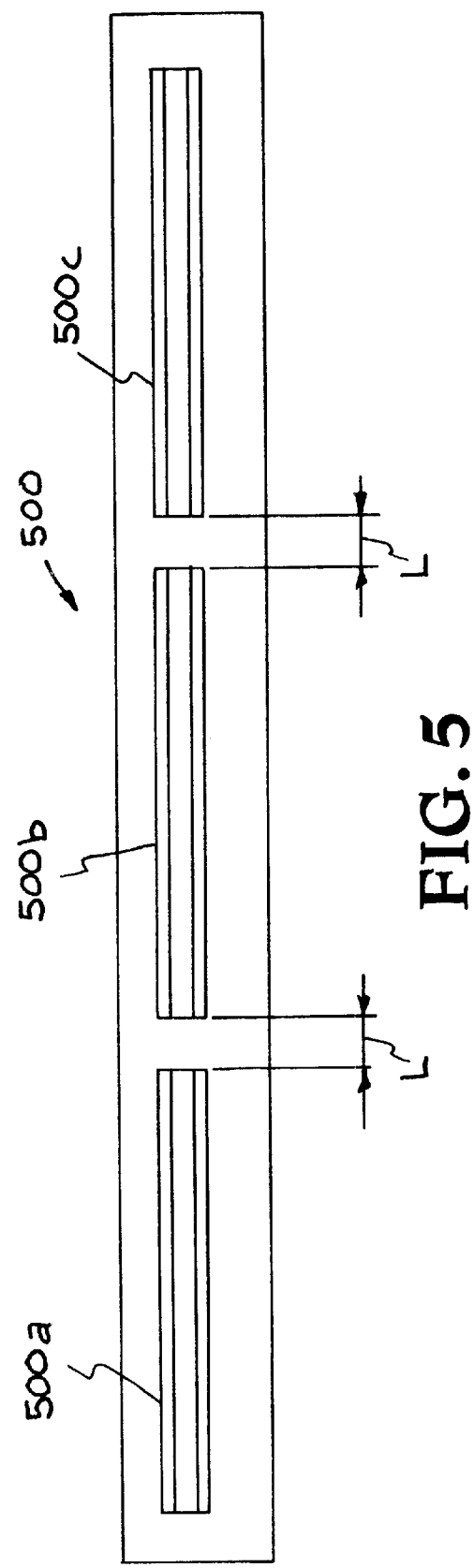
FIG. 5 illustrates a plan view of a divided scale assembly.

FIG. 5 illustrates a third and preferred embodiment which enables measurement of travel outside the commercial range of existing scales. Current scales are limited in length due to the cost of manufacturing a scale of any great length with the appropriate exacting accuracy. The third embodiment uses a plurality of scales 500a, 500b and 500c together with only a slight scale gap L between each of the scales to form a scale assembly 500 having an extended length as shown in detail in FIG. 5. Although three scales are shown in FIG. 5, the scale assembly 500 may also be modified to include two scales or a number greater than three. Each of the scales 500a–c are similar in design to scale 200 with center gradations bordered on each side by orthogonal gradations.

A problem addressed by this third embodiment is the discontinuity and phasing of measurement as sensors pass over the scale gaps L as shown in FIG. 5. This difficulty may be overcome by using a pair of sensors to perform the same function as a single sensor in previous embodiments. The third embodiment functions in a manner very similar to the first and second embodiments, except that, the sensor pairs work synchronously to adjust for the scale gaps L. The sensor pairs will be separated by a predetermined distance (i.e., greater than the length of gap L) so that as one sensor passes over a gap L the other sensor of the pair may still be monitoring the gradations on scale assembly 500 which contains scales 500a–500c to determine the position of the rigid body 101. As a first sensor of a sensor pair passes over the distance of the interface L, the position information from the other sensor of the pair is used. This method of passing the monitoring function back and forth between a pair of sensors may be termed for the purposes of this disclosure an "electronic handshake". The controller 170 receives the data from each pair of sensors and utilizes software containing a standard algorithm in the controller 170 to calculate the displacement position. This method produces a seamless string of position data and overcomes the problems caused by the interfaces of the plurality of scales. Using this method, there is conceivably no limit to the number of scales that may be used in the scale assembly 500.

Figure 4:
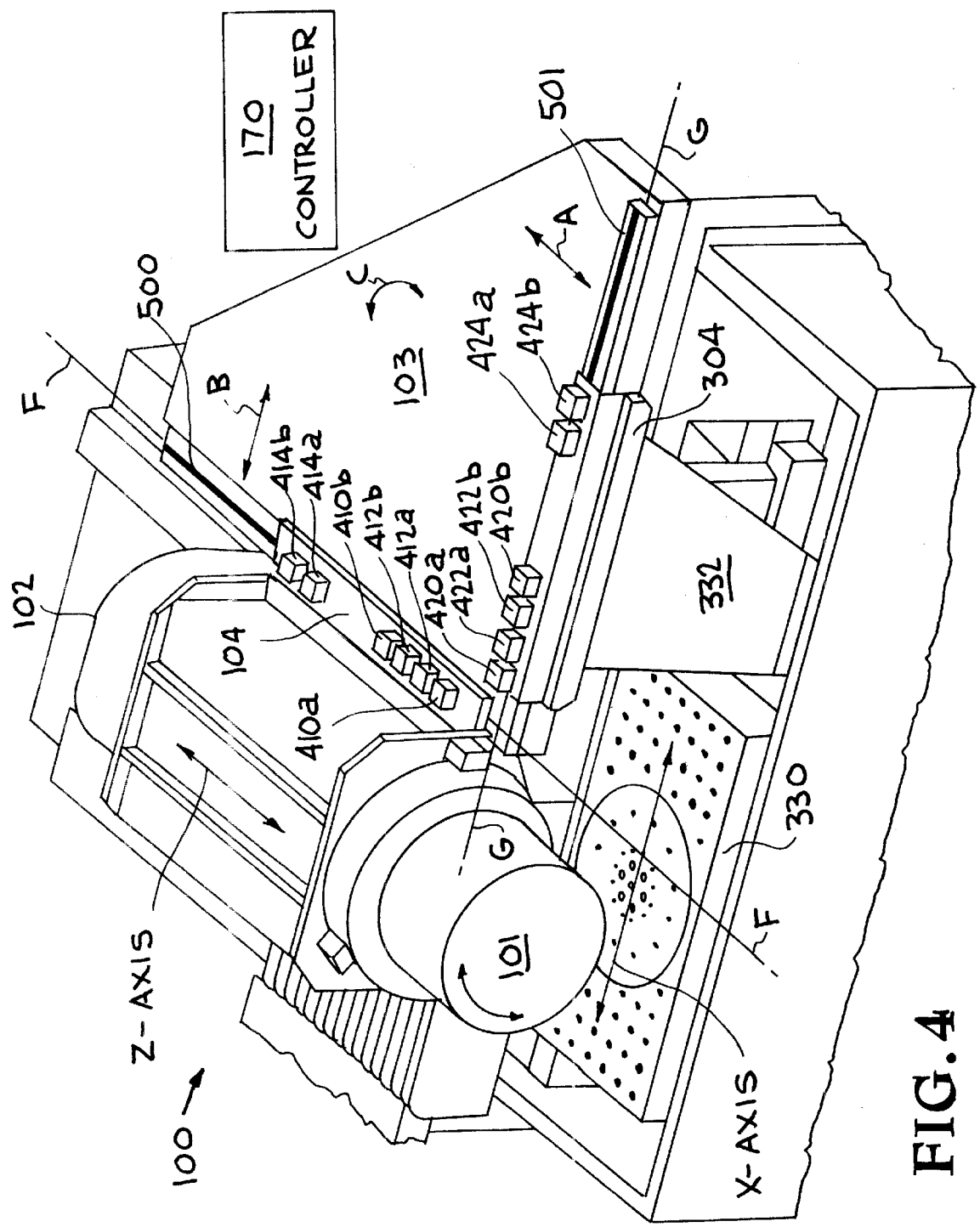
FIG. 4 illustrates a perspective view of a third embodiment of the present invention.

FIG. 4 discloses a first pair of sensors 410a–410b which measure the linear displacement of the effective point 410c along first scale assembly 500. Second and third sensor pairs 412a–412b and 414a–414b measure the departure from straightness and angular displacement of the effective point 410c from the F axis along first scale assembly 500. Sensor pairs 420a–420b measure the linear displacement of the effective point 420c along the second scale assembly 501. Second scale assembly 501 is similar in structure to first scale assembly 500. Sensor pairs 422a–422b and 424a–424b measure the departure from straightness and angular displacement of the effective point 420c from the second scale assembly 501 along the G axis.

The disclosed embodiments may be used under atmospheric conditions (i.e., 101 325 pascals) to achieve high precision measurement. For example, measurements may be taken on a nanometric ($10^{-9}$ meters) level. The ability to operate in non-vacuum conditions (i.e., above $10^{-2}$ pascal) allows the disclosed embodiments to be implemented in a more inexpensive manner than systems which use a laser inside a vacuum to achieve precision measurements.

An advantage of the disclosed embodiments is the capability to measure displacement, angle and straightness in one, inexpensive system.

The foregoing is illustrative of the present invention and is not to be construed as limiting thereof. The invention is defined by the following claims, with equivalents of the claims to be included therein.

What is claimed is:

1. A system comprising:
   a first periodic measurement scale assembly substantially aligned with a first axis; and
   a first plurality of sensors positioned substantially proximate to said first periodic measurement scale assembly, said first plurality of sensors including a pair of sensors spaced from each other along the first axis and configured to cooperatively measure at least one of departure from straightness of a first effective point from the first axis and angular displacement of the first effective point from the first axis.

2. The system of claim 1, wherein said first plurality of sensors includes at least one sensor configured to measure linear displacement of the first effective point along the first axis.

3. The system of claim 1, further comprising:
a second periodic measurement scale assembly substantially aligned with a second axis substantially orthogonal to said first axis; and
a second plurality of sensors positioned substantially proximate to said second periodic measurement scale assembly, said second plurality of sensors including at least one sensor configured to measure linear displacement of a second effective point along the second axis, and a pair of sensors spaced from each other along the second axis and configured to cooperatively measure at least one of departure from straightness of the second effective point from the second axis, and angular displacement of the second effective point from the second axis.

4. The system of claim 2, wherein only one of said first plurality of sensors is configured to measure linear displacement of the first effective point along the first axis.

5. The system of claim 1, wherein the position of said first effective point indicates a position of a functional point of a rigid body.

6. The system of claim 2, wherein said first periodic measurement scale assembly has a first plurality of marks extending in a first direction substantially parallel to the first axis, and a second plurality of marks extending in a second direction substantially orthogonal to the first axis, the second plurality of marks for use in the cooperative measurement of the departure from straightness and angular displacement by the pair of sensors.

7. The system of claim 6, wherein said plurality of first marks extending in said first direction are bounded on both sides by the second plurality of marks extending in the second direction.

8. The system of claim 1, wherein said first plurality of sensors are mounted on a first assembly.

9. The system of claim 8, wherein said first assembly is mounted on a first mounting member; and
said first mounting member adapted to attach to a rigid body.

10. The system of claim 1, wherein said sensors are transducers.

11. A measuring device comprising:
a first scale assembly having a plurality of first periodic measurement scales substantially aligned with a first axis; and
a first plurality of pairs of sensors positioned in substantial proximity to said first scale assembly, said first plurality of pairs of sensors including a first pair of sensors spaced from each other along the first axis and configured to cooperatively measure departure from straightness of a first effective point from the first axis.

12. The measuring device of claim 11, wherein said first plurality of pairs of sensors includes a second pair of sensors spaced from each other along the first axis and configured to cooperatively measure linear displacement of the first effective point along the first axis and a third pair of sensors spaced from each other along the first axis and configured to cooperatively measure angular displacement of the first effective point from the first axis.

13. The measuring device of claim 11, wherein each of said first periodic measurement scales are separated by a gap.

14. The measuring device of claim 13, wherein each of said first plurality of pairs of sensors are configured to perform a handshaking function as one of each of the pairs of sensors passes over each of said gaps.

15. The measuring device of claim 13, wherein one of each of said first plurality of pairs of sensors are configured to monitor said plurality of first periodic measurement scales as the other pair of said first plurality of pairs of sensors passes over said gaps.

16. The measuring device of claim 11, further comprising:
a second scale assembly having a plurality of second periodic measurement scales substantially aligned with a second axis substantially orthogonal to the first axis; and
a second plurality of pairs of sensors positioned substantially proximate to said second plurality of periodic measurement scales, said second plurality of pairs of sensors including a fourth pair of sensors spaced from each other along the second axis and configured to cooperatively measure linear displacement of a second effective point along the second axis, a fifth pair of sensors spaced from each other along the second axis and configured to cooperatively measure departure from straightness of the second effective point from the second axis, and a sixth pair of sensors spaced from each other along the second axis and configured to cooperatively measure angular displacement of the second effective point from the second axis.

17. The measuring device of claim 12, wherein each pair of said first and third pairs of sensors are separated by a distance of greater than about six inches.

18. The measuring device of claim 12, wherein each pair of said first and third pairs of sensors are separated by a distance greater than the distance from the effective point to a functional point of a rigid body.

19. The measuring device of claim 11, further comprising:
a control system containing software programmed to perform an offset operation on data collected from said first plurality of pairs of sensors.

20. The measuring device of claim 11, further comprising:
a control system containing software programmed to perform a handshake function during periods when one of said first plurality of pairs of sensors is located over a gap in the plurality of first periodic measurement scales.

21. A position measuring device comprising:
a plurality of first periodic measurement scales substantially aligned with a first axis; and
a first plurality of sensors positioned substantially proximate to said plurality of first periodic measurement scales, said first plurality of sensors including at least one sensor configured to measure linear displacement of a first effective point along the first axis, and a pair of sensors spaced from each other along the first axis and configured to cooperatively measure departure from straightness of the first effective point from the first axis, and angular displacement of the first effective point from the first axis.

22. A machine tool comprising:

a first scale assembly having a first periodic measurement scale aligned with a first axis; and a firs plurality of sensors positioned in proximity to said first scale assembly, said first plurality of sensors including a pair of sensors spaced from each other along the first axis and configured to cooperatively measure at least one of departure from straightness of a first effective point from the first axis and angular displacement of the first effective point from the first axis.

23. The machine tool of claim 22, further comprising:

a second scale assembly having a second periodic measurement scale substantially aligned with a second axis substantially orthogonal to said first axis; and a second plurality of sensors positioned substantially proximate to said second scale assembly, said second plurality of sensors including at least one sensor configured to measure linear displacement of a second effective point along the second axis, and a pair of sensors spaced from each other along the second axis and configured to cooperatively measure at least one of departure from straightness of the second effective point from the second axis, and angular displacement of the second effective point from the second axis.

24. The machine tool of claim 23, wherein said first and second periodic measurement scale assemblies are substantially orthogonal.

25. A method comprising:

measuring at least one of departure from straightness of a first effective point from a first axis and angular displacement of the first effective point from the first axis, by cooperatively utilizing a pair of sensors spaced from each other along the first axis and positioned substantially proximate a first scale assembly substantially aligned with said first axis.

26. The method of claim 25, further comprising:

measuring linear displacement of the first effective point along the first axis by using at least one sensor positioned substantially proximate said first scale assembly.

27. The method of claim 26, further comprising:

measuring linear displacement of a second effective point along a second axis using at least one sensor positioned substantially proximate a second scale assembly;

measuring at least one of departure from straightness of the second effective point from the second axis and angular displacement of the second effective point from the second axis, by cooperatively using a pair of sensors spaced from each other along the second axis and positioned substantially proximate said second scale assembly.

28. The method of claim 26, wherein said first scale assembly has gradations aligned with said first axis and gradations substantially orthogonal to said first axis.

29. A method of determining the position of a rigid body comprising:

measuring linear displacement of a first effective point along a plurality of measurement scales substantially aligned along a first axis by cooperatively using a first pair of sensors positioned substantially proximate said plurality of measurement scales; and measuring at least one of departure from straightness of the first effective point from the first axis and angular displacement of the first effective point from the first axis, by cooperatively using a second pair of sensors spaced apart from each other along the first axis and positioned substantially proximate said plurality of measurement scales.

30. The method of claim 29, wherein said first, and second pairs of sensors are substantially aligned with each other.

31. The method of claim 29, wherein said plurality of measurement scales have gradations substantially aligned with said first axis and gradations substantially orthogonal to said first axis.

32. The method of claim 29, further comprising:

performing a handshake function when one of said first and second pairs of sensors passes over one of a plurality of gaps located between said plurality of measurement scales.

33. The method of claim 29, further comprising:

performing an offset calculation in a controller to relate the position of the first effective point to a functional point on said rigid body.

34. An apparatus comprising:

means for measuring at least one of departure from straightness and angular displacement of a first effective point from a first axis by cooperatively using a pair of sensors spaced from each other along said first axis and positioned substantially proximate a first scale assembly substantially aligned with said first axis.

35. The apparatus of claim 34, further comprising:

means for measuring linear displacement of the first effective point along the first axis by using at least one sensor positioned substantially proximate said first scale assembly.

36. The apparatus of claim 34, further comprising:

means for measuring linear displacement of a second effective point along a second axis by using at least one sensor positioned substantially proximate a second scale assembly; and means for measuring at least one of departure from straightness and angular displacement of the second effective point from the second axis by cooperatively using a pair of sensors positioned substantially proximate said second scale assembly.

37. The apparatus of claim 34, wherein said first scale assembly has gradations aligned with said first axis and gradations substantially orthogonal to said first axis.

38. A measuring device comprising:

means for measuring linear displacement of a first effective point along a plurality of measurement scales aligned along a first axis by using a first pair of sensors positioned substantially proximate said plurality of measurement scales; and means for measuring at least one of departure from straightness of the first effective point from the first axis and angular displacement of the first effective point from the first axis by cooperatively using a second pair of sensors positioned substantially proximate said plurality of measurement scales.

39. The measuring device of claim 38, wherein said first, and second pairs of sensors are substantially aligned with each other on a first assembly.

40. The measuring device of claim 38,
wherein said plurality of measurement scales have gradations substantially aligned with said first axis and gradations substantially orthogonal to said first axis.

41. The measuring device of claim 38, wherein the first pair of sensors are configured to perform a handshake function when one of said first pair of sensors passes over one of a plurality of gaps located between said plurality of measurement scales.

42. The measuring device of claim 38, further comprising:
means for performing an offset calculation in a controller to relate the position of the first effective point to a functional point on a rigid body.

43. A system comprising:
first means for measuring a position of a rigid body relative to a reference body; and
second means for measuring a position of an object relative to the reference body, with said object configured to act upon said rigid body
wherein said second means is configured to compensate for errors in the position of the rigid body relative to the object.

44. A system comprising:
a first scale assembly substantially aligned with a first axis;
a second scale assembly substantially aligned with a second axis substantially orthogonal to the first axis;
a first slide assembly having at least one sensor and designed to travel along and substantially proximate to said first scale assembly;
a second slide assembly separate from the first slide assembly, and having at least one sensor and designed to travel along and substantially proximate to said second scale assembly; and
a control system configured to utilize data from said at least one sensor on said second slide assembly to compensate for errors in the positioning of a first effective point on the first slide assembly.

45. The system of claim 44,
wherein said first effective point is designed to correspond to the position of a functional point on a rigid body.

46. The system of claim 45,
wherein said second slide assembly is designed to indicate the position of a tool operating on said rigid body.

47. The system of claim 44,
wherein the control system is configured to utilized data from said at least one sensor on said first slide assembly to compensate for errors in the positioning of a second effective point on the second slide assembly.

48. A system comprising:
a first scale assembly having a plurality of first periodic measurement scales substantially aligned with a first axis;
a first plurality of pairs of sensors positioned substantially proximate to said first scale assembly said first plurality of pairs of sensors including at least one sensor configured to measure linear displacement of the first effective point along the first axis, and a pair of sensors spaced apart from each other and configured to cooperatively measure at least one of departure from straightness of a first effective point from the first axis and angular displacement of the first effective point from the first axis;
a second scale assembly having a plurality of periodic measurement scales aligned with a second axis;
a second plurality of pairs of sensors positioned substantially proximate to said second plurality of periodic measurement scales, said second plurality of pairs of sensors including at least one sensor configured to measure linear displacement of a second effective point along the second axis, and a pair of sensors spaced apart from each other and configured to cooperatively measure at least one of departure from straightness of the second effective point from the second axis, and angular displacement of the second effective point from the second axis; and
wherein said second plurality of pairs of sensors are configured to compensate for errors in the positioning of a rigid body.

* * * * *